(12) United States Patent
Köhler

(10) Patent No.: US 7,206,441 B2
(45) Date of Patent: Apr. 17, 2007

(54) METHOD FOR DETERMINING AN OBJECT FUNCTION

(75) Inventor: Thomas Köhler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 784 days.

(21) Appl. No.: 10/387,828

(22) Filed: Mar. 13, 2003

(65) Prior Publication Data

US 2003/0179918 A1 Sep. 25, 2003

(30) Foreign Application Priority Data

Mar. 15, 2002 (DE) ................. 102 11 485

(51) Int. Cl.
*G06K 9/00* (2006.01)
(52) U.S. Cl. ................................... 382/131
(58) Field of Classification Search ............. 382/131
See application file for complete search history.

(56) References Cited

U.S. PATENT DOCUMENTS

| | | | | |
|---|---|---|---|---|
| 5,355,310 | A * | 10/1994 | Brunner ................. | 382/275 |
| 5,414,623 | A * | 5/1995 | Lu et al. ............... | 382/131 |
| 5,625,190 | A * | 4/1997 | Crandall ............... | 250/363.03 |
| 5,907,594 | A * | 5/1999 | Lai ....................... | 378/4 |
| 5,982,845 | A * | 11/1999 | Sidoti et al. ......... | 378/4 |
| 6,281,681 | B1 * | 8/2001 | Cline et al. .......... | 324/310 |
| 6,410,919 | B1 * | 6/2002 | Nickles ................ | 250/363.03 |
| 6,434,214 | B1 * | 8/2002 | Kawai et al. ........ | 378/4 |

OTHER PUBLICATIONS

Kochunov, Peter V., Ho-Ling Liu, Trevor Andrews, Jia-Hong Gao, Peter T. Fox, and Jack L. Lancaster. "A B0 Shift Correction Method Based on Edge RMS Reduction for EPI fMRi". Journal of Magnetic Resonance Imaging: 2000. vol. 12. pp. 956-959.*

Hudson, H. Malcolm and Richard S. Larkin. "Accelerated Image Reconstruction using Ordered Subsets of Projection Data". IEEE Transactions on Medical Imaging: Dec. 1994. vol. 13. No. 4. pp. 601-609.*

Press, William H., Saul A. Teukolsky, William T. Vetterling, and Brian P. Flannery. "Numerical Recipes in C": 1988. Cambridge University Press, Second Edition.*

(Continued)

*Primary Examiner*—Bhavesh M Mehta
*Assistant Examiner*—Damon Conover

(57) ABSTRACT

The invention relates to a method in which object functions are generated from projections of an object by means of an iterative reconstruction algorithm with determination of approximation images. This method is used in, for instance, image-generating systems for producing images of object functions. Image-generating systems of this kind are generally used when images of an object are to be generated without cutting or destroying the object itself in the process. In the process, projections of the object are acquired from different projection directions from a maximum angular range. In an iteration cycle, an approximation image of the object function and a projection are used to calculate, using the reconstruction algorithm, a new approximation image which produces a further new approximation image in the subsequent iteration cycle in conjunction with a projection from a different projection direction. In successive iteration cycles, projections are used whose projection directions differ by an angle that derives from the division of the maximum angular range in accordance with the golden section.

9 Claims, 8 Drawing Sheets

OTHER PUBLICATIONS

Figure 1:
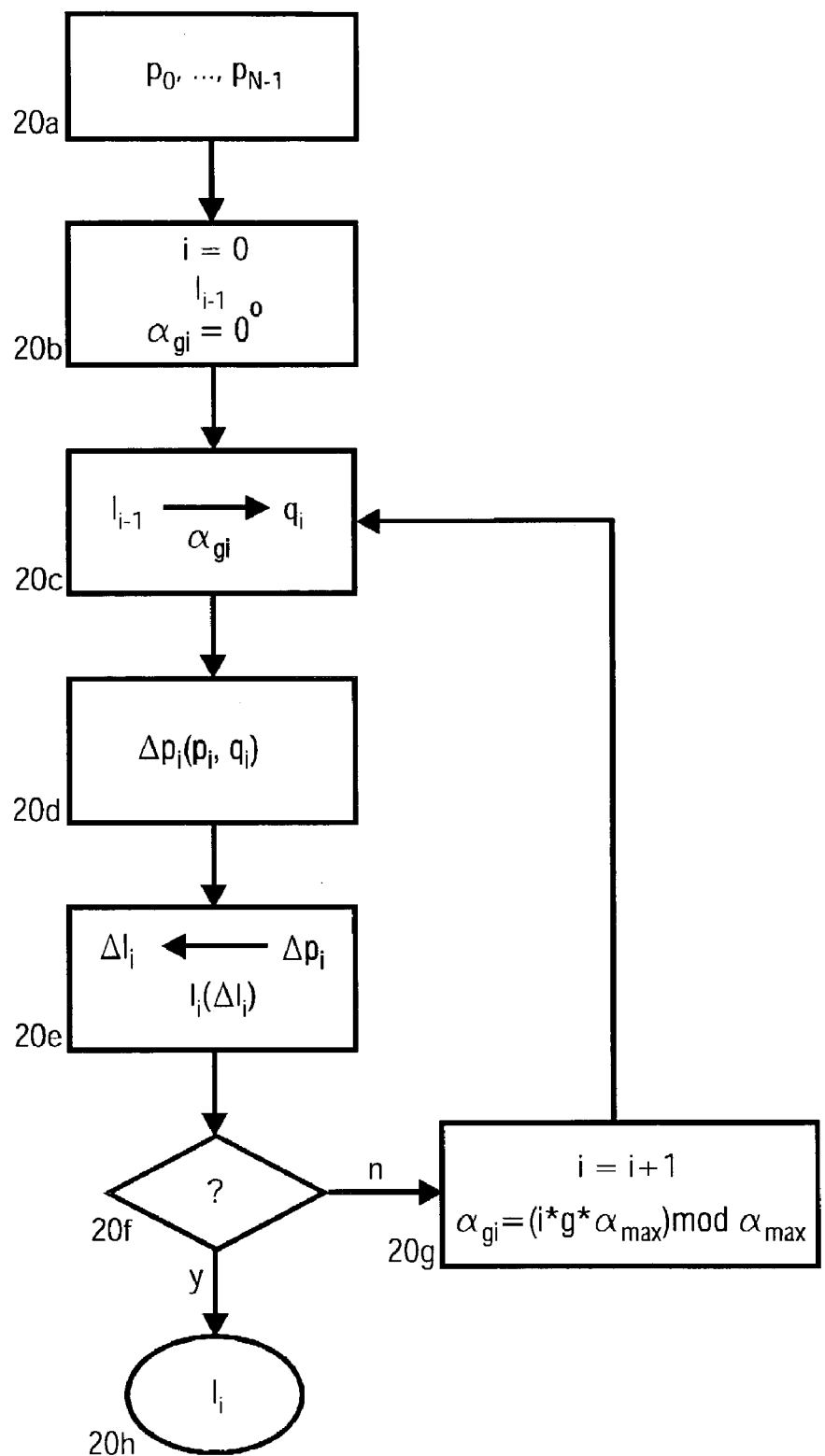

Hudson, H. Malcolm, et al.; Accelerated Image Reconstruction Using Ordered Subsets of Projection Data; IEEE Transaction on Medical Imaging, vol. 13, No. 4, Dec. 1994, pp. 601-609.

Herman, Gabor T., et al.; Algebraic Reconstruction Can Be Made Computationally Efficient; IEEE Transactions on Medical Imaging, vol. 12, No. 3, Sep. 1993, pp. 600-609.

* cited by examiner

METHOD FOR DETERMINING AN OBJECT FUNCTION

The invention relates to a method in which an object function is determined from projections of an object while using an iterative reconstruction algorithm. This method can be used in systems for generating images of object functions. The invention also relates to a system in which a method of this kind is used for determining an object function, and to a computer-program product with which a data processing unit can execute this method.

Image-generating systems of this kind are generally used when images, for instance, sectional images or volumetric images of an object, are to be generated without destroying the object in the process. First an object function of the object is determined, which can then be shown as an image. In principle, an object function represents the distribution of object properties, in medicine, for instance, object properties represent the spatial distribution of the attenuation of X-rays, the tissue-specific accumulation of radiant substances or the local distribution of nuclear magnetization. In order to determine the object function, projections of the object from different projection directions are acquired, and the object function is reconstructed from these with the aid of a reconstruction algorithm. Known medical devices that undertake a process of this kind are X-ray computed tomography apparatus, devices used in nuclear medicine that are based on SPECT and PET processes, or magnetic resonance tomography apparatus.

The article by H. M. Hudson and R. S. Larkin "Accelerated Image Reconstruction Using Ordered Subsets of Projection Data", published in "IEEE Transactions On Medical Imaging, Vol. 13, No. 4, December 1994, p. 601 et seq.", describes a recursive reconstruction algorithm for the reconstruction. In each iteration cycle, an approximation image of the object function is determined from a projection and the previously calculated approximation image. With each iteration cycle performed, the quality increases of the approximation images which thus converge in the course of the reconstruction towards the object function. In each iteration cycle, a projection is used, the projection direction of which differs from the projection direction of the projection used in the previous iteration cycle: starting from a first projection, the projection whose projection direction is perpendicular to the projection direction of the first projection is used as the second projection. The third and the fourth projection used are those whose projection directions are centrally located between the projection direction of the first and the second projection, etc.

It is an object of the invention to find a method for image-producing systems, which exhibits improvements as compared with existing systems.

This object is achieved by means of a method for determining an object function from projections of the object acquired from various projection directions by means of an iterative reconstruction algorithm, in which an iteration cycle comprises the following:

determination of a projection $q_i$ by forward-projection of an approximation image $I_{i-1}$ in the projection direction $\alpha_{gi}$ of an actually acquired projection $p_i$;

determination of corrective information from the differences between the projections $p_i$ and $q_i$;

determination of a new approximation image $I_i$ from the approximation image $I_{i-1}$ and the back-projected corrective information;

definition of a new projection $p_i$ with the projection direction $\alpha_{gi}$ which differs, at least by approximation, by the angle $\alpha_g = g \cdot \alpha_{max}$ from the previous projection direction $\alpha_{gi}$, $\alpha_{max}$ representing the entire angular range used in creating the projections, and g representing the ratio of the golden section; and execution of the iteration cycle repeatedly until an abort condition is fulfilled.

Projections of an object are acquired from different projection directions, from which projections an object function of the object is reconstructed with the aid of an iterative reconstruction algorithm. In an iteration cycle, a new approximation image is produced, with the reconstruction algorithm, from an approximation image of the object function and a projection, which new approximation image, together with a projection from a different projection direction, provides a further new approximation image in the subsequent iteration cycle. In order to reconstruct the object function, the iteration cycle is repeated sufficiently often for an abort condition to be fulfilled; in the course of the reconstruction the approximation images converge more and more towards the object function.

During implementation of an iteration cycle, the method assigns to the reconstruction algorithm the projections whose projection direction is displaced by a specific angle relative to the projection direction of the projection that was used in the previous iteration cycle. This angle corresponds, at least by approximation, to the angle that derives from the division of the entire angular range used for all acquisitions in the ratio of the golden section. The golden section is known in detail from basic mathematical general knowledge and specialist mathematical literature. It derives from a specific harmonic aspect ratio of $g=1-((\sqrt{5}-1)/2) \approx 0.382$. If the arc of a complete circle is divided by the golden section, a division of the circle into two segments at an angle of $\alpha_g = g \cdot 360° \approx 137.52°$ is derived. Alternatively, the golden section also derives from the complementary aspect ratio as $g'=(\sqrt{5}-1)/2$. Since both g and g' can be used with complete equivalence for the invention, exclusively $g=1-((\sqrt{5}-1)/2) \approx 0.382$ will be assumed in the text below.

In certain cases, it is not necessary to plot projections of the object under investigation from the entire angular range of a complete circle. In a computed tomography apparatus system as further explained below, for instance, it is irrelevant whether a projection is plotted at an angle of $\beta$ or $\beta+180°$. In a system of this kind, it is therefore sufficient to plot projections within, for instance, a maximum angular range of 180°. This gives rise to a division of the maximum angular range at an angle of $\alpha_g \approx 0.382 \cdot 180° = 68.75°$.

Through the use of this method, a projection that contains, in particular, a great deal of new information for the reconstruction of the object function, is used in every iteration cycle. This results in the approximation images converging especially rapidly towards the object function in the course of the reconstruction. As a result, in comparison with known processes, the quality of the approximation image as regards the object function is better for the same number of iteration cycles, or a specific quality of the approximation image can be achieved with fewer iteration cycles and less calculation time. Moreover, this process is especially simple to integrate into existing systems, since the selection of the projection to be used is to be determined by addition of a fixed angular increment $\alpha_g = g \cdot \alpha_{max}$ to the projection direction of the most recently used projection.

When, in the definition of a new projection, the projection of an actually acquired projection which is the closest to the calculated projection direction is defined as the new projection direction, the method in accordance with aspects of the invention can also be used in existing systems, even if the projection directions of the actually acquired projections do not coincide with the projection directions determined in accordance with the invention. If the actually acquired projections are distributed homogeneously over the entire angular range, the error between an acquired and a calculated projection direction is especially small if the total number N of projections is a Fibonacci number.

A system for producing an object function of an object or object range from projections acquired from different projection directions, which system includes a data-processing unit for undertaking an iterative reconstruction algorithm comprising determination of a projection $q_i$ by forward-projection of an approximation image $I_{i-1}$ in the projection direction $\alpha_{gi}$ of an actually acquired projection $p_i$ and determination of corrective information from the differences between the projections $p_i$ and $q_i$. A determination id made of a new approximation image $I_i$ from the approximation image $I_{i-1}$ and the back-projected corrective information and definition is made of a new projection $p_i$ with the projection direction $\alpha_{gi}$ which differs, at least by approximation, by the angle $\alpha_g = g \cdot \alpha_{max}$ from the previous projection direction $\alpha_{gi'}$, $\alpha_{max}$ representing the entire angular range used in creating the projections, and g representing the ratio of the golden section. The iterative reconstruction is executed repeatedly until an abort condition is fulfilled. The method in accordance with this aspect of the invention can be used in many systems that generate object functions from projections by means of an iterative reconstruction algorithm; the advantage then derives from the faster convergence of the approximation images towards the object function to be determined. Especially in image-producing systems, which represent object functions as images, for instance, as sectional views or volumetric views, or supply them for further processing, the use of the method ensures an enhanced system performance.

It is used especially advantageously in systems that can be used inter alia in medicine, such as a system operating by the PET method, a system operating by the SPECT method, an X-ray system or a magnetic resonance tomography apparatus. Especially the performance of systems that, according to the current level of knowledge, exclusively use iterative reconstruction algorithms for determining an object function is enhanced through use of the method.

If the data processing unit of a system as mentioned above is designed so that it can be programmed, the use of the method in accordance with the invention in systems of this kind is enabled by a computer programming product as claimed in claim 9.

The invention will be further described with reference to embodiments shown in the drawings, to which, however, the invention is not restricted.

Figure 2A:
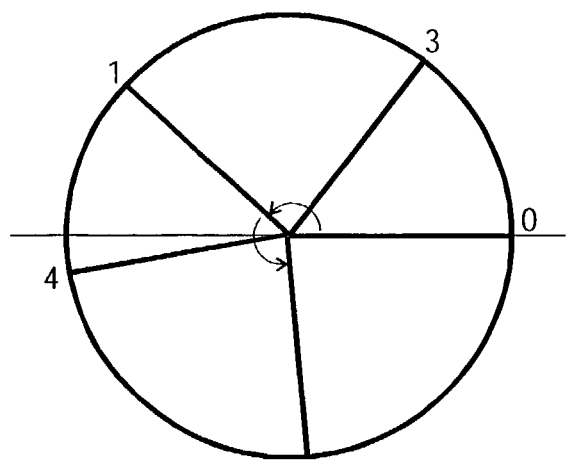
Figure 2B:
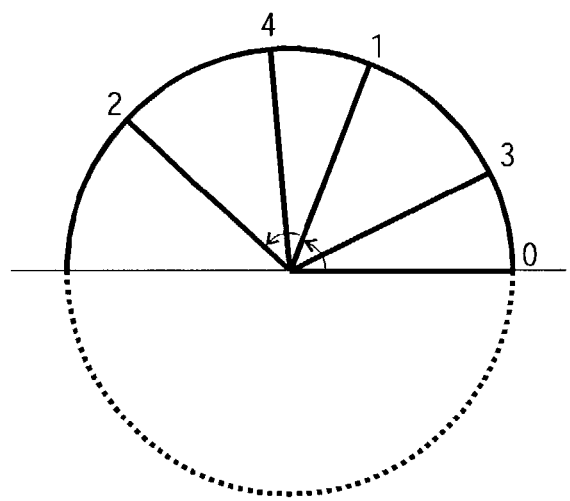
Figure 2C:
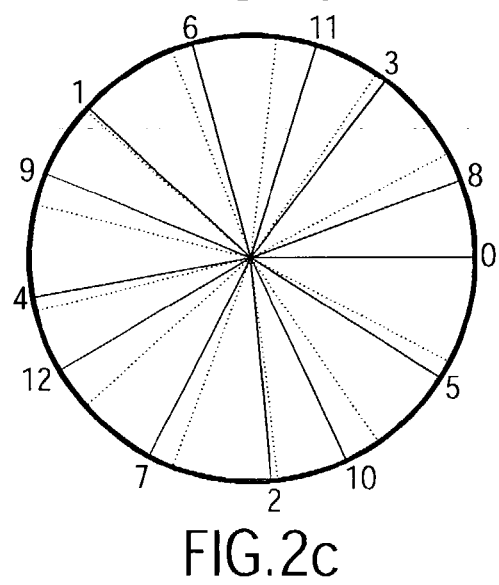
Figure 3:
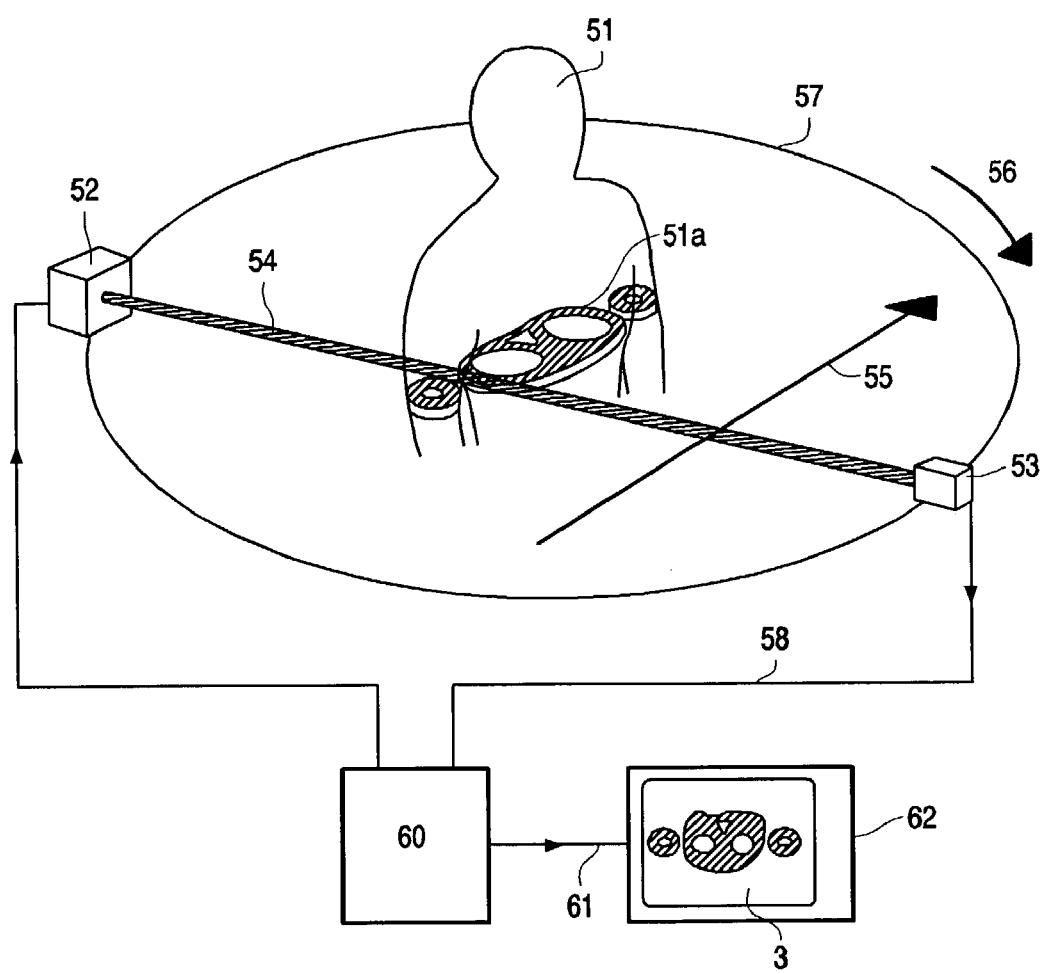
Figure 4:
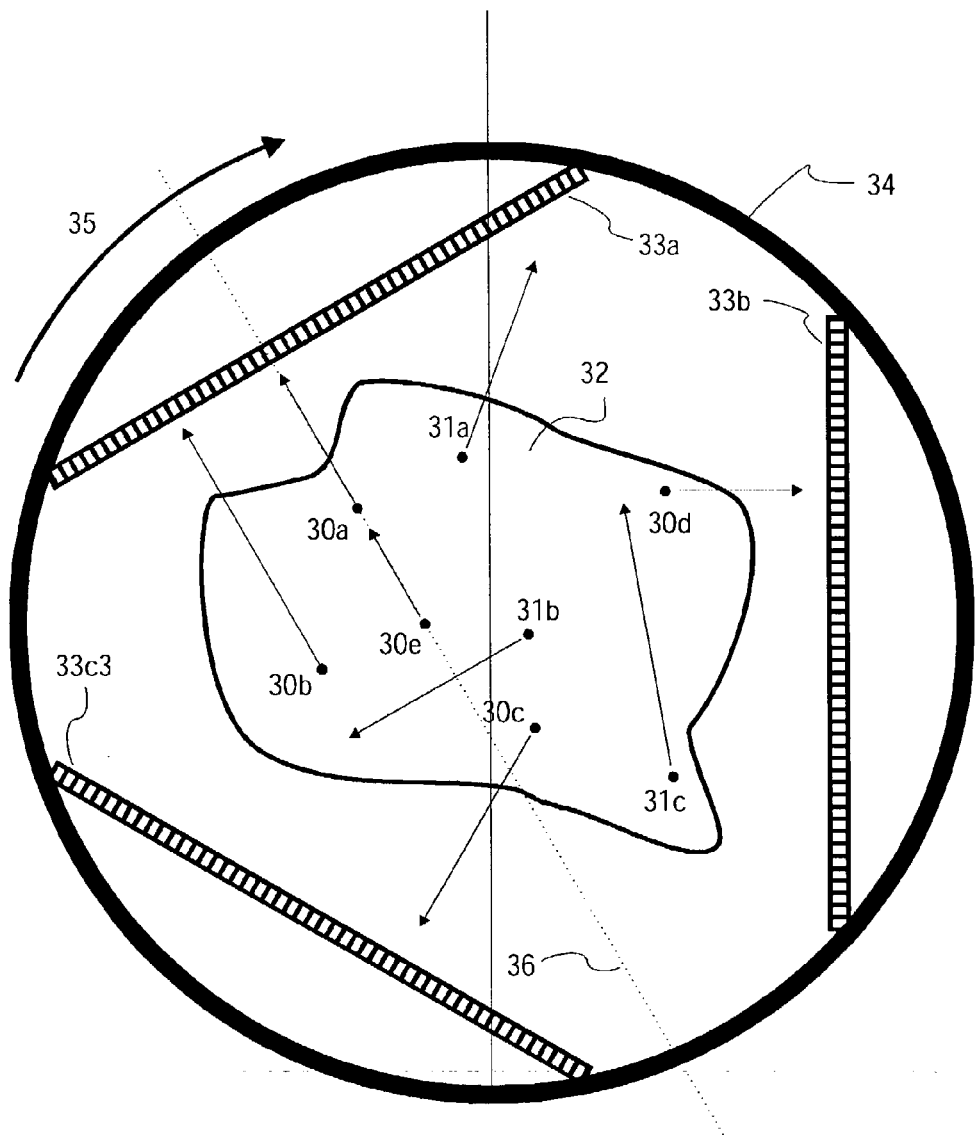
Figure 5:
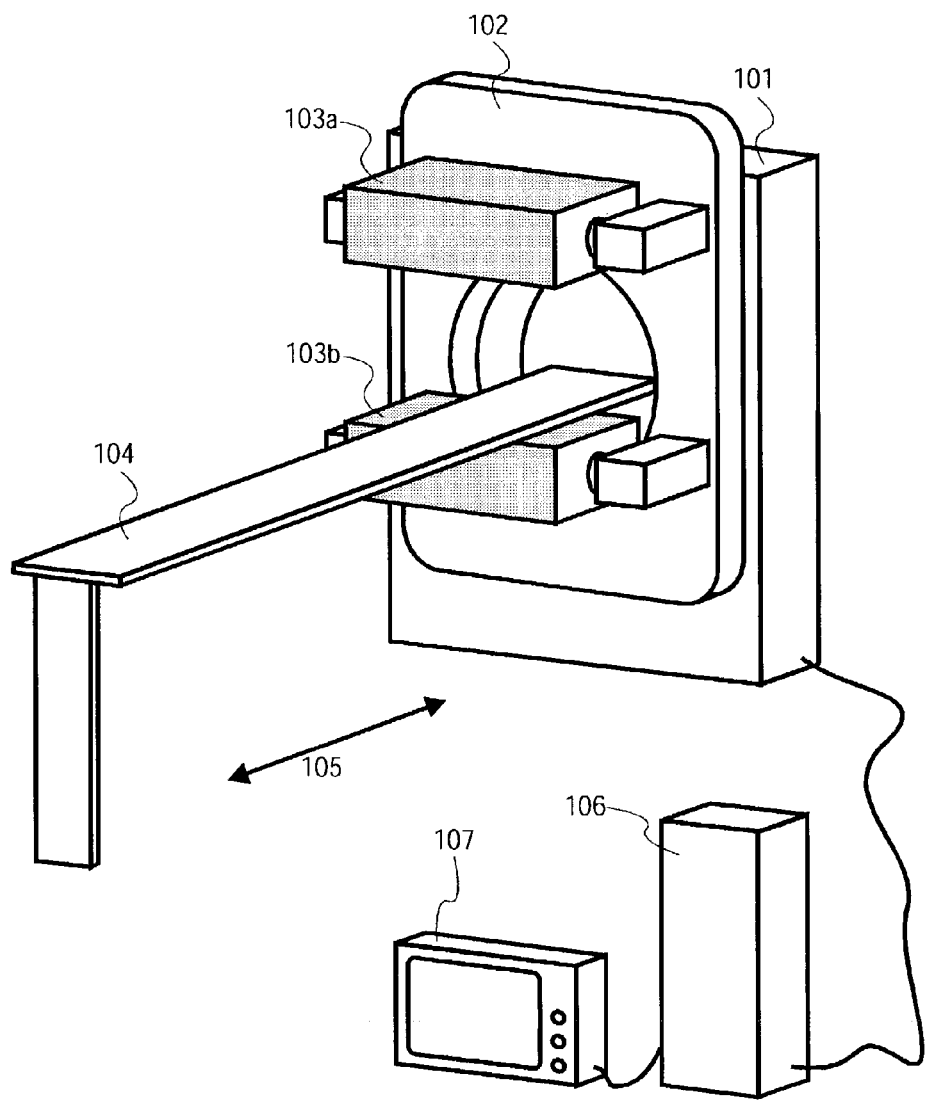
Figure 6:
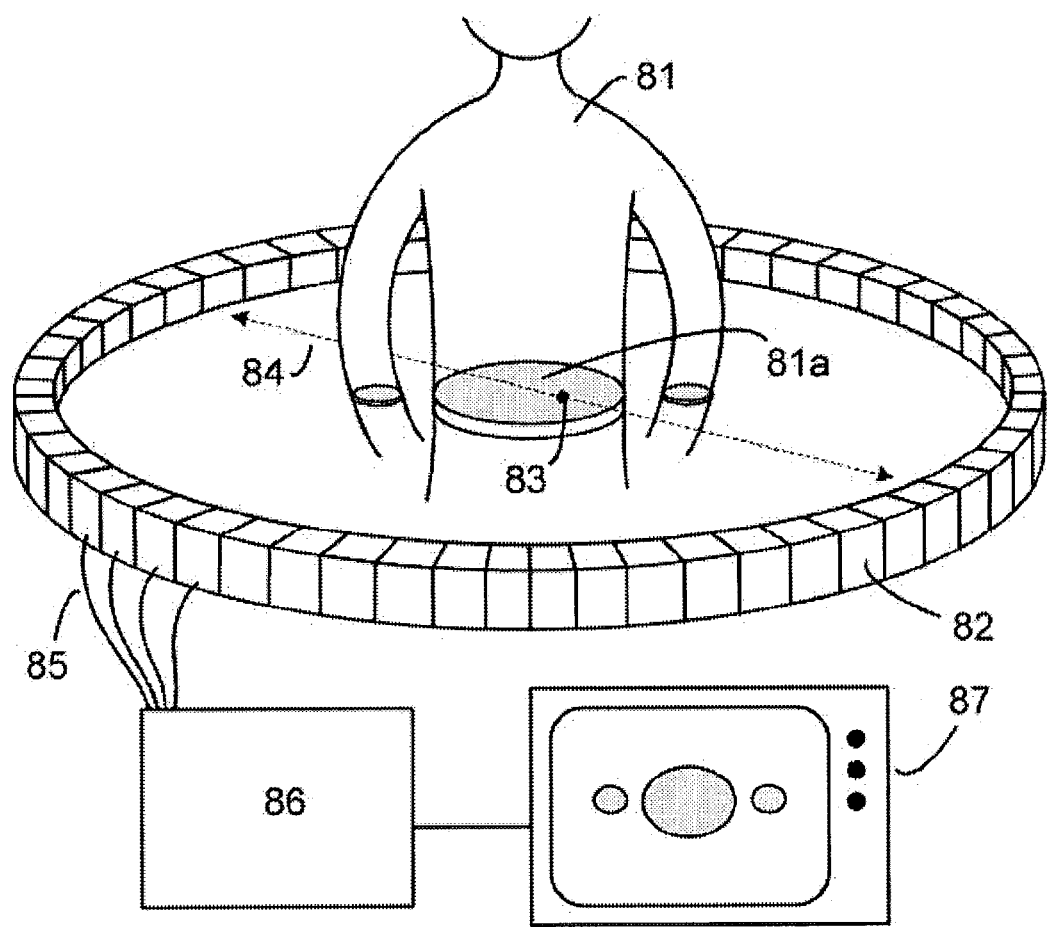
Figure 7:
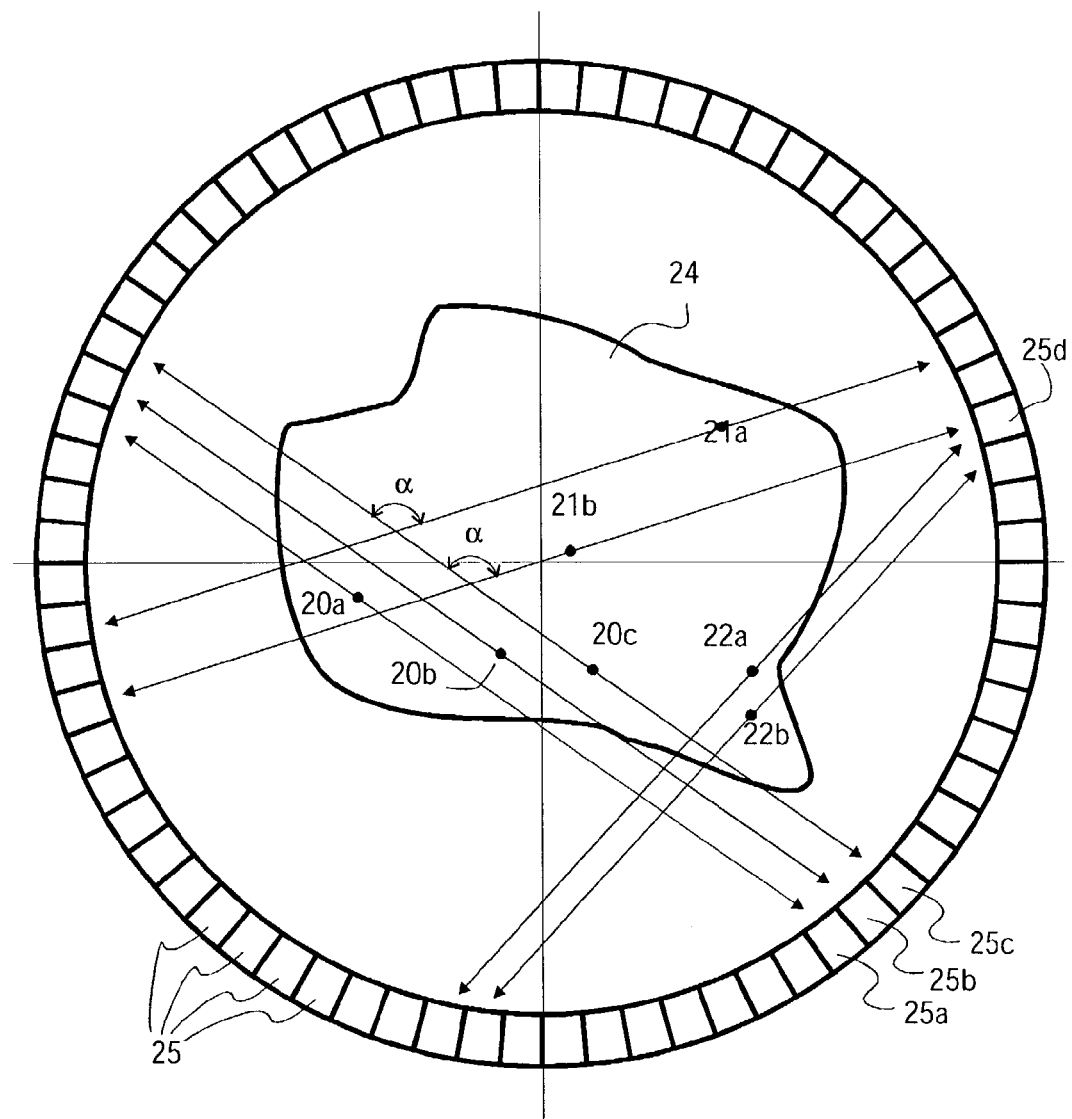
Figure 8:
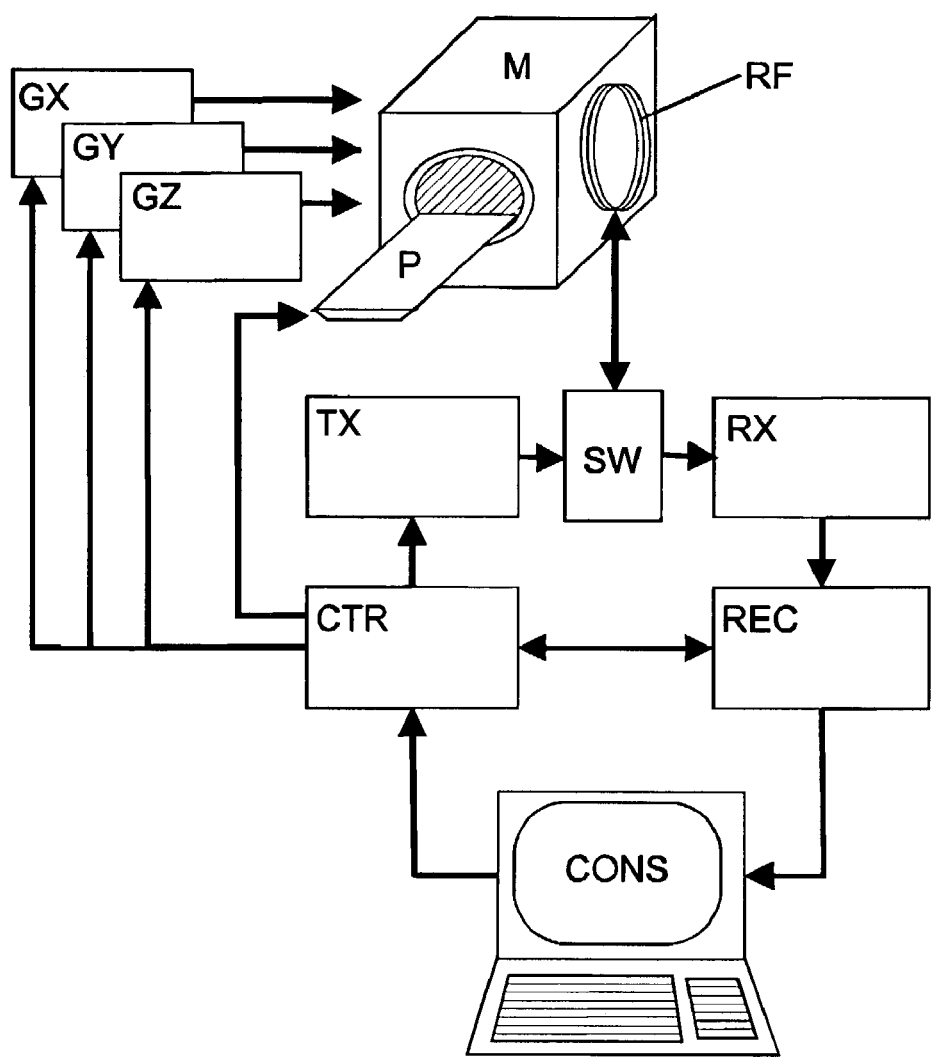

FIG. 1 shows a flowchart of an iterative reconstruction algorithm,

FIG. 2a shows the first projection directions in the case of a total acquisition range of 360°, FIG. 2b shows the first projection directions in the case of a total acquisition range of 180°, FIG. 2c shows 13 projection directions of homogeneously distributed projections and 13 projection directions of projections distributed in accordance with the invention, FIG. 3 shows schematically the structure of a computed tomography system, FIG. 4 shows schematically how projections are produced in a SPECT system, FIG. 5 shows schematically the structure of a SPECT system, FIG. 6 shows schematically the structure of a PET system, FIG. 7 shows schematically how projections are produced in a PET system, and FIG. 8 shows schematically the structure of an MR system.

Turning now to FIG. 1, the general steps for an example of an iterative reconstruction algorithm. In step 20a, N projections $p_0, \ldots p_{N-1}$ of the object to be imaged are acquired from different projection directions. A projection corresponds to a data set of line integrals of the object function, the integration lines being straight lines. So-called parallel projection is characterized in that all straight lines lie parallel to one another. So-called fan projection, in which the straight lines are arranged in a fan shape and intersect at a (fictitious) point, is characterized by an angle of aperture (angle between the two outermost straight lines) and a median line (bisecting line of the angle of aperture).

Step 20b serves for initializing the components used in the iteration. A numerator is initialized with i=0, a first projection direction with $\alpha_{g(i=0)}=0°$ and a first approximation image $I_{(i=0)-1}$ with initialization values, for instance, 0.

At step 20c, a first iteration cycle begins. From the approximation image $I_{i-1}$, a projection $q_i$ is calculated, the projection direction of which corresponds to the projection direction $\alpha_{gi}$ of a measured projection $p_i$. In this so-called forward projection, a data set of line integrals is calculated from the approximation image $I_{i-1}$ along lines that correspond as far as possible to the integration lines of the actual projection $p_i$. In the case of parallel projections, the integration lines pass through the approximation image $I_{i-1}$ from the projection direction $\alpha_{gi}$. In the case of fan projections, the median line that is characteristic of fan projection runs through the approximation image $I_{i-1}$ from the projection direction $\alpha_{gi}$.

In step 20d, a corrective projection $\Delta p_i$ is determined from the calculated projection $q_i$ and the measured projection $p_i$. The determination of the corrective projection is dependent on the reconstruction algorithm used. A known reconstruction algorithm is the ART algorithm (Algebraic Reconstruction Techniques) which is described in detail in, for instance, the article by G. T. Hermann and L. B. Meyer "Algebraic Reconstruction Techniques—Can Be made Computationally Efficient", published in "IEEE Transactions On Medical Imaging, Vol. 12, No. 3, September 1993, p. 600 et seq." In equation (6), an iteration step is cited mathematically. Here it is shown that the corrective projection should be calculated from the difference between the actual projection and the calculated projection of the forward-projected approximation image. Another known reconstruction algorithm is the so-called OS-EM algorithm (Ordered Subsets—Expectation Maximization), which is explained in detail in, for instance, the article by H. M. Hudson and R. S. Larkin "Accelerated Image Reconstruction Using Ordered Subsets of Projection Data", published in "IEEE Transactions On Medical Imaging, Vol. 13, No. 4, December 1994, p. 601 et seq." Equations (1) and (2) contain the detailed mathematical description, which shows that the corrective projection should be calculated from the quotient of the actual projection and the calculated projection of the forward-projected approximation image.

In step 20e, this corrective projection $\Delta p_i$ is back-projected, as a result of which a corrective image $\Delta I_i$, comprising parallel straight lines in the case of parallel projections, for instance, is created. The individual points of a straight line in the corrective image all exhibit the same value, which is determined in such a way that a line integral along this straight line produces precisely the value of the corrective projection $\Delta p_i$ at the appropriate the location. This process of back-projection is also known as "smearing" of a line-integral value along a straight line.

A new approximation image $I_i$ of the object function is determined from the approximation image $I_{i-1}$ and the corrective image $\Delta I_i$. This determination is, in turn, dependent on the reconstruction algorithm used. In the case of the ART algorithm, which is described in the above-mentioned article, the new approximation image is determined from the addition of the old approximation image and the corrective image, the corrective image being multiplied in advance by a relaxation parameter which may assume values from the range from virtually 0 to 2, for instance. In the OS-EM algorithm, which is described in the above-mentioned article, the new approximation image is determined from the multiplication of the old approximation image by the corrective image.

In step 20f, an abort condition is checked. An abort condition of this kind is to be considered in a general sense and may be, for instance that:
The difference between the projections $p_i$ and $q_i$ is sufficiently small.
The quality of the approximation image with respect to the object function is adequate.
The number of iteration cycles reaches a defined value.
The duration of the reconstruction has reached a specific time.
A user terminates the reconstruction
Other . . .

If the abort condition is not yet fulfilled, there follows in step 20g an increase of the numerator i=i+1, thus defining a new projection direction $\alpha_{g(i=i+1)}$. As a result, the projection $p_{i=i+1}$, the projection direction of which is offset by an angle $\alpha_g = g \cdot \alpha_{max}$ in relation to the projection direction of the projection $p_i$ used previously, is used in the next iteration cycle in the steps 20c, 20d and 20e. This is explained in greater detail with reference to FIG. 2a. Let the projection used for the previous steps 20c to 20e be $p_i = p_0$, represented by projection 0, the projection direction of which is $\alpha_{g0} = 0°$. As a result of the increase of i=i+1, the projection direction $\alpha_{g(i=i+1)} = \alpha_{g1}$ of the projection 1 used subsequently is determined such that the projection direction $\alpha_{g1}$ is offset by an angle $\alpha_g = g \cdot \alpha_{max}$ in relation to the projection direction $\alpha_{g0}$ of the projection 0. With $\alpha_{max} = 360°$ as shown here, we derive for $\alpha_{g(i=i+1)} = \alpha_{g1} \approx (1 \cdot 360°) \bmod 360° = 137.52°$, as a result of which, in the following steps, 20c to 20e, the projection $p_1$ having the projection direction $\alpha_{g1} \approx 137.52°$ is used. Once these steps have been executed, i=i+1 is again set in step 20g, and the next projection direction $\alpha_{g2}$ of the projection 2 is defined as $\alpha_{g2} \approx (2 \cdot g \cdot 360°) \bmod 360° = 275.04°$. After the next iteration cycle, $\alpha_{g3} \approx (3 \cdot g \cdot 360°) \bmod 360° = 52.56°$ is set for the next projection 3, etc.

The way in which the reconstruction is undertaken is explained with reference to FIG. 2b for a system in which the N projections are plotted not from the angular range of a complete circle, but from an angular range of $\alpha_{max} = 180°$. The various projection directions are then calculated from $\alpha_{gi} = (i \cdot g \cdot 180°) \bmod 180°$ for $0 \leq i < N-1$. The projection 0 used in the first iteration cycle was acquired from the projection direction $\alpha_{g0} = 0°$, the projection 1 used in the second iteration cycle was acquired from the projection direction $\alpha_{g(i=i+1)} = \alpha_{g1} \approx (1 \cdot g \cdot 180°) \bmod 180° = 68.76°$, the projection 2 used in the third iteration cycle was acquired from the projection direction $\alpha_{g(i=i+1)} = \alpha_{g2} \approx (2 \cdot g \cdot 180°) \bmod 180° = 137.52°$, the projection 3 was acquired from $\alpha_{g(i=i+1)} = \alpha_{g3} \approx (3 \cdot g \cdot 180°) \bmod 180° = 26.28°$, etc.

The general formula derived for the sequence to be used for the N projections of an object from the various angles $\alpha_{gi}$ is then $\alpha_{gi} = (i \cdot g \cdot \alpha_{max}) \bmod \alpha_{max}$, where g is the ratio of the "golden section" and $\alpha_{max}$ defines the angular range within which all projections are acquired. The integer numerator i runs from $0 \leq i < N-1$. The operation a=bmodc is a general representation for $a = b - (b \div c) \cdot c$, where $(b \div c)$ is defined as the integer component of the actual result of the division b/c (the result of a division can, in general, be represented as a sum of an integer component and a residue: b/c=d+e, where d is integral and $0 \leq e < 1$).

The iteration cycle of FIG. 1 with the steps 20c, 20d, 20e, 20f and 20g is completed repeatedly until the abort condition is fulfilled in the step 20f. In step 20h, the reconstruction is completed, and the approximation image $I_i$ that is then available corresponds with sufficient accuracy to the object function of the object and may be shown forthwith as an image.

FIG. 2c shows, for a maximum angular range of $\alpha_{max} = 360°$, an example of the difference between projections that have been acquired from homogeneously distributed projection directions and projections whose projection directions have been determined in accordance with the invention. The 13 projection directions represented by dotted lines are homogeneously distributed over the entire maximum angular range, and the 13 projection directions represented by solid lines are projection directions determined in accordance with the invention. It is apparent that the projection direction for each of the actually acquired projections is located in the vicinity of a projection direction determined in accordance with the invention:

| Projection direction number | Actual projection direction | Projection direction in accordance with the invention |
|---|---|---|
| 0 | 0° | 0° |
| 1 | 138.46° | 137.52° |
| 2 | 276.92° | 275.04° |
| . . . | . . . | . . . |
| 11 | 83.08° | 72.72° |
| 12 | 221.54° | 210.24° |

It is thus possible to use in accordance with the invention, in the individual iteration cycles, the projections actually acquired. The greatest error between an actual and a calculated projection direction occurs for the projection direction 12, with $\Delta \alpha_{g12} \approx 221.54° - 210.24° = 11.3°$. Since 13 is a Fibonacci number, this error is especially small as compared with the errors that occur in a total of 12 or 14 projections. In real systems, of course, depending on the system options, significantly more projections than the 13 shown here, for instance 233 or 377, are used. The greater the number of projections actually acquired, the smaller the errors between the actually acquired and the calculated projection directions.

A Fibonacci number is an element from the so-called Fibonacci sequence, in which the first two elements are 1, and all further elements are formed from the sum of the two previous elements. The first elements (numbers) in the Fibonacci sequence are 1, 1, 2, 3, 5, 8, 13, 21, 34, 55, 89, 144, 233, 377, 610, 987.

Below, the options for using the method in accordance with the invention in an X-ray computed tomography system are explained. To this end, the general creation of projections is first explained, followed by the principle of their use. FIG. 3 shows the schematic diagram of an X-ray computed tomography system. The sectional view of the section 51a through an object 51 is to be produced. To this end, an X-ray source 52 produces a narrow X-ray beam 54, which enters into the object 51, penetrates the object 51 along a straight line within the sectional plane of section 51*a*, is attenuated in accordance with the constitution of the object 51, and detected by an X-ray detector 53 on leaving the object. The attenuation that takes place during the penetration represents a measure of the integral over the local distribution of the attenuation along the penetration line. In order to measure the entire sectional range, further integrals are measured along parallel straight lines; to this end the X-ray source 52 and the detector 53 are each offset slightly by the same amount in the direction of the arrow 55. A parallel projection of the section 51*a* of the object 51 has now been obtained from a set of attenuation integrals.

In a next step, the X-ray source 52 and the X-ray detector 53 are offset by a small angle, around 1° for instance, on a circular path 57 in the direction of the arrow 56. The next parallel projection is then produced by the same procedure as previously described. Subsequently, a number of parallel projections is produced until the X-ray tube and the detector have completed a rotation of at least 180°.

The data from the projections travels via a connection 58 into a data-processing and control unit 60, which also controls the X-ray source 52 and the positioning facilities for the X-ray tube and the detector which are not shown here. Here, after the parallel projections have been produced, a sectional view 63 of the section 51*a* is reconstructed with the aid of the method in accordance with the invention in that, during the execution of an iteration cycle, the projection whose projection direction is offset, at least by approximation, by an angle of $\alpha_g \approx 0.382 \cdot 180° = 68.75°$ from the projection direction of the projection that was used in the previous iteration cycle, is assigned to the reconstruction algorithm.

The principle of the operating mode of a computed tomography apparatus described here is couched in very general terms and serves essentially for explaining how projections are obtained and an object function reconstructed. Modern computed tomography apparatus generally produce fan projections rather than parallel projections. Systems that rotate helically around the object during production of the projections are also known, producing many slightly offset projections which can be processed by the so-called cone beam CT process into volumetric images of the object. The method in accordance with the invention can also be used accordingly in systems of this kind.

A method for producing sectional views that is known in nuclear medicine is the SPECT (Single Photon Emission Computed Tomography) sectional-view method. FIG. 4 shows the schematic structure of a device for producing SPECT sectional views. Three detectors 33*a*, 33*b* and 33*c* are arranged in a circular mount 34, offset from one another by an angle of 120°. Each detector 33*a*, 33*b* and 33*c* is equipped with sensors which are provided for detecting gamma quanta (γ-quantum) incident on the detector 33*a*, 33*b* and 33*c* from a defined projection direction. In FIG. 4, the projection direction is essentially perpendicular to the surface of the relevant detector 33*a*, 33*b* and 33*c*, as a result of which γ quanta that are incident on the relevant detector essentially perpendicularly to the surface of the detector 33*a*, 33*b* or 33*c* are detected. A projection direction may be formed, for instance, in that a collimator, not shown here, is located in front of every sensor, which collimator, owing to its tube-like structure, allows only X-ray beams that run essentially parallel to the center axis of the tube to pass through to the relevant sensor.

The basis of image-generating systems in nuclear medicine is the fact that the object to be imaged is self-radiating. The γ quanta to be detected therefore arise not from an external source, but from the object itself. To this end, a patient is injected with, for instance, a metabolic preparation, marked with specific unstable nuclides, which concentrates in the body tissue-specifically or function-specifically, for instance, in locations with certain metabolic activities. While the preparation decays, decay quanta emitting from the body arise and are measured and used for producing a sectional view. The SPECT process uses radio nuclides which emit an individual γ quantum as they decay. The γ quanta leave the object in a straight line, disregarding scattering effects.

FIG. 4 is a sectional view of the object 32 to be imaged. By way of example, at the locations marked with dots, 30*a*, 30*b*, 30*c*, 30*d*, 30*e*, 31*a*, 31*b*, 31*c*, radio nuclides are decaying, thus causing γ quanta which leave the object 32 in the direction of the respective arrows. If a propagation direction roughly corresponds to the projection direction of one of the detectors 33*a*, 33*b* or 33*c*, the corresponding γ quantum is detected by a sensor of the corresponding detector. The γ quantum arising at the location 30*a* as a result of decay hits the surface of the detector 33*a* virtually perpendicularly and is detected by a sensor. The same sensor of the detector 33*a* detects the γ quantum arising at the location 30*e*, since its propagation direction is the same as the propagation direction of the γ quantum arising at the location 30*a*. The sum of all the γ quanta detected by this sensor forms a line integral along the line 36 via the γ quanta that are propagating along the line 36 in the direction of the detector 33*a*. This line integral thereby forms a datum of a projection. The further data for this projection are formed by the line integrals of the remaining sensors of the detector 33*a*, the lines of the line integrals running in parallel with the line 36. A parallel projection is created.

All γ quanta that leave the object 32 in the projection direction of one of the detectors 33*a*, 33*b* and 33*c* at a particular time, therefore contribute to the data set of a parallel projection. The γ quanta arising at the locations 30*a*, 30*e* and 30*b* contribute to the data set of the parallel projection that is momentarily being created by the detector 33*a*. They quantum arising at the location 30*c* contributes to the data set of the parallel projection that is momentarily being created by the detector 33*c*. The γ quantum arising at the location 30*d* contributes to the data set of the parallel projection that is momentarily being created by the detector 33*b*. The γ quanta arising at the locations 31*a*, 31*b* and 31*c* do not contribute to any data set, since their propagation direction does not coincide with any projection direction of any of the detectors 33*a*, 33*b* or 33*c*.

The arrangement shown in FIG. 4 produces a parallel projection simultaneously with each of the detectors 33*a*, 33*b* and 33*c*. In a subsequent step, the circular mount 34 of the detectors is rotated in the direction of the arrow 35 by a small angle. Three further parallel projections, differing from the previous ones, are now produced. The mount 34 is then again rotated by a small angle in the direction of the arrow 35, and three further projections are formed. When the mount 34 has been rotated by a total of 120°, a complete set of parallel projections of the object 32 has been produced.

By contrast with the functional representation of FIG. 4, FIG. 5 shows the structure of a device for producing a sectional view with the SPECT sectional-view process. By comparison with the arrangement in FIG. 4, this device is equipped with two detectors, rather than three, as a result of which only two, rather than three, projections can be created simultaneously. The two detectors 103a and 103b are secured on a mount 102, which is connected to a carrier 101 and pivot-mounted. Concentrically with the rotation axis of the mount 102, a circular opening is located in the carrier 101 and in the mount 102, through which opening a table 104 can be pushed so as to be parallel with the rotation axis of the mount 102. The patient undergoing investigation, who has been injected at the start of the investigation with a metabolic preparation marked with specific unstable nuclides, lies on this table, though this is not shown here. The table 104 is moved in relation to the carrier 101 in the direction of the arrow 105 in such a way that the section through the patient to be imaged lies in the projection directions of the detectors 103a and 103b. The data from the parallel projections measured by the detectors is taken to a data-processing unit 106 which reconstructs a sectional view from this data and displays it on a monitor 107.

In order to reconstruct the sectional view, an iterative reconstruction algorithm is used in the data-processing unit, the projection to be used being defined in accordance with the invention in each iteration cycle.

A further process known from nuclear medicine for creating sectional views is the PET (Positron Emission Tomography) sectional-view process. In a similar way to the SPECT process, a patient is injected with a metabolic preparation marked with specific, unstable nuclides, which accumulates tissue-specifically or function-specifically. The radio nuclides of light atomic nuclei used decay and emit positrons. A positron of this kind is rapidly decelerated by scattering processes on adjacent atoms, and captured by a shell electron. The positron and electron then form a positronium for a brief moment before their mass is converted into two γ quanta in the process known as annihilation. The two γ quanta then fly apart in precisely opposite directions, leave the patient and can be detected by appropriate sensors.

FIG. 6 shows schematically the structure of a device for producing a sectional view with the PET process. The patient or the object under investigation 81 is located in a detector ring, comprising individual sensors 82. The plane formed by the ring cuts the object 81, for instance, in the sectional plane 81a. At the location 83, the decay process described above takes place, two γ quanta then leaving the object 81 in opposite directions along the doubleheaded arrow 84. The individual sensors of the detector are connected, via connections 85, to a data-processing unit 86, which evaluates the signals from the sensors. The sectional view created is then displayed on a monitor 87.

FIG. 7 shows parts of a device of this kind in a plan view. The object 24 is again located in a ring-shaped detector, comprising individual sensors 25, 25a, 25b, 25c, 25d. At each of the locations 20a, 20b, 20c, 21a, 21b, 22a and 22b, the above-described process takes place; two γ quanta then leaving the object 24 along the corresponding doubleheaded arrows, and hit the detector. If the two γ quanta are measured by two opposing sensors within a specific time, the location of origin of the γ quanta is defined at a position on the connecting line between these two sensors. If the γ quanta originate precisely in the center between two sensors, the paths of each of the γ quanta to a sensor are of equal length, and the γ quanta are detected simultaneously. If one of the paths is shorter, one γ quantum will be detected slightly earlier than the other. This gives rise to a time window in which two sensors both have to detect a γ quantum in order for these γ quanta to be assigned to the same origination process. Furthermore, the time between two successive origination processes has to be long enough for it to be distinguished from the time of the time window.

Let us now consider the origination location 20a with the associated doubleheaded arrow, which represents the propagation direction of the γ quanta originating there. Further γ quanta, which originate on the line of the doubleheaded arrow and also leave the object along the doubleheaded arrow, are detected in the same way as the γ quanta from the location 20a by the sensors. The sum of all γ quanta detected in this way gives rise to a line integral through the detected γ quanta along the connecting line of the sensors. This line integral may be regarded as the datum of a data set of a projection. Those line integrals through detected γ quanta in which the γ quanta leave the object 24 on paths parallel with this doubleheaded arrow are used as further data of this data set. These are, for instance, the γ quanta that originated at the locations 20b and 20c. The γ quanta that originated at the locations 21a and 2b, for instance, belong to the data set of another projection. The γ quanta that originated at the locations 22a and 22b belong to the data set of a third projection.

In FIG. 6, a sectional view is produced in the data-processing unit 86 with the aid of an iterative reconstruction algorithm. The parallel projections produced are assigned to the individual iteration cycles in accordance with the invention.

Another system for producing images of object functions is the magnetic resonance tomography apparatus. It is known that magnetic resonance tomography is a spectral imaging process in which localization of the nuclear magnetization takes place on the basis of the associated resonance frequency through the use of a spatially inhomogeneous magnetic field (magnetic field gradient). It is generally the case that, to produce the image, the magnetic resonance signal is acquired under the influence of a suitable sequence of high-frequency and gradient pulses in the time domain, as a voltage that is induced in a coil surrounding the investigation area. The actual image reconstruction then takes place by Fourier transformation of the time signals into space. The scanning of the reciprocal "k-space", determining the volumetric range to be imaged and the image resolution, is specified by means of the number, the time interval, the duration and the strength of the gradient and high-frequency pulses used. The projections $P(r,\phi)$ of the transverse magnetization on the corresponding field gradient can be determined from the Fourier-transformed time signals $m(k,\phi)$ measured in the k-space as $m(k,\phi)=\int P(r,\phi)e^{ikr}\partial r$ or $P(r,\phi)=\frac{1}{2\pi}\int m(k,\phi)e^{ikr}\partial k$.

All points of a straight line passing through the origin in the k-space thus lie on a straight line passing through the origin in space. If the method in accordance with the invention is used for reconstructing the object function in space with an iterative reconstruction algorithm, the projections $P(r,\phi_{gi})$ along a straight line through the origin, for which $\phi_{gi}$ is fixed and r varies in accordance with the points along the straight line, are used in an iteration cycle i. To determine these points, the measured values of the Fourier-transformed points from the k-space are used in accordance with the above formula. In a subsequent iteration cycle i=i+1, those projections $P(r,\phi_{gi})$ along another straight line through the origin for which, at least by approximation, $\phi_{gi}=(i\cdot g\cdot\phi_{max})\text{mod}\phi_{max}$ are used. As a result, in successive iteration cycles, the projection directions of the projections differ in accordance with the invention. Since, as has just been shown, the projections used in a magnetic resonance tomography apparatus are not created directly, but only after a transformation, suitable sequences for the acquisition of the nuclear spin signals must be selected in order to carry out the method in accordance with the invention.

FIG. 8 shows schematically an MR device that is suitable for undertaking the method in accordance with the invention. In the core of the installation is a main magnet M, which produces an essentially homogeneous, stationary magnetic field with a flux density of e.g. 1.5 tesla in an investigation area. The magnet M is usually a superconducting electromagnet. A patient table P on which a patient lies for an investigation can be moved into the magnet M. The field direction of the magnet M typically runs parallel to the longitudinal direction of the patient table P. An arrangement of gradient coils GX, GY, GZ is also provided, being supplied with power via gradient amplifiers which are not shown. The gradient pulses required for the various pulse sequences can thus be generated in any direction in space in the investigation area. An arrangement of high-frequency coils RF serves for applying high-frequency pulses to the investigation area and receiving MR signals from the investigation area. To this end, the arrangement of coils RF can be switched back and forth between a high-frequency power transmitter TX and a receiver RX. The transmitter TX is driven by a control unit CTR, which also controls the gradient coils GX, GY and GZ in order to generate the required pulse sequences. The control unit CTR is also used to vary the position of the patient table P. A reconstruction unit REC digitalizes and stores the MR signals supplied by the receiver RX and then undertakes the reconstruction therefrom, using the method in accordance with the invention, object functions of the investigation area. The reconstruction unit REC is connected to an operator console CONS, which has a monitor on which image data of the reconstructed object functions are displayed. The console CONS simultaneously serves for operating the entire arrangement and initiating the desired pulse sequences. To this end, the console CONS is also connected to the control unit CTRL. The method in accordance with the invention is implemented by appropriate programming of the reconstruction unit REC.

The invention claimed is:

1. A method for determining an object function from projections of the object acquired from different projection directions by means of an iterative reconstruction algorithm, in which an iteration cycle comprises the following:
   determination of a projection $q_i$ by forward-projection of an approximation image $I_{i-1}$ in the projection direction $\alpha_{gi}$ of an actually acquired projection $p_i$;
   determination of corrective information from the differences between the projections $p_i$ and $q_i$;
   determination of a new approximation image $I_i$ from the approximation image $I_{i-1}$ and the back-projected corrective information;
   definition of a new projection $p_i$, with the projection direction $\alpha_{gi}$ which differs, at least by approximation, by the angle $\alpha_g = g \cdot \alpha_{max}$ from the previous projection direction $\alpha_{gi}$, $\alpha_{max}$ representing the entire angular range used in creating the projections, and g representing the ratio of the golden section; and
   execution of the iteration cycle until an abort condition is fulfilled.

2. A method as claimed in claim 1, wherein during the definition of a new projection the projection direction of an actually acquired projection which is closest to the calculated projection direction is defined as the new projection direction.

3. A method as claimed in claim 2, wherein the total number of actually acquired projections is a Fibonacci number.

4. A system for producing an object function of an object or object range from projections acquired from different projection directions, the system includes a data-processing unit for undertaking an iterative reconstruction algorithm comprising:
   determination of a projection $q_i$ by forward-projection of an approximation image $I_{i-1}$ in the projection direction $\alpha_{gi}$ of an actually acquired projection $p_i$;
   determination of corrective information from the differences between the projections $p_i$, and $q_i$;
   determination of a new approximation image $I_i$ from the approximation image $I_{i-1}$ and the back-projected corrective information;
   definition of a new projection $p_i$ with the projection direction $\alpha_{gi}$ which differs, at least by approximation, by the angle $\alpha_g = g \cdot \alpha_{max}$ from the previous projection direction $\alpha_{gi}$, $\alpha_{max}$ representing the entire angular range used in creating the projections, and g representing the ratio of the golden section; and
   execution until an abort condition is fulfilled.

5. A system as claimed in claim 4, comprising an X-ray detector and adapted to determine object functions of the object or object region by means of the PET process.

6. A system as claimed in claim 4, comprising an X-ray detector adapted to determine object functions of the object or the object region by means of the SPECT process.

7. A system as claimed in claim 4, comprising an X-ray source and an X-ray detector and adapted to acquire projections of the object or the object region by means of X-rays.

8. A system as claimed in claim 4, adapted to determine object functions of the object or the object region by means of magnetic resonance tomography.

9. A computer-readable medium encoding instructions which when executed by a processor performs processing operations including:
   determining a projection $q_i$ by forward-projection of an approximation image $I_{i-1}$ in the projection direction $\alpha_{gi}$ of an actually acquired projection $p_i$;
   determining corrective information from the differences between the projections $p_i$ and $q_i$;
   determining a new approximation image I, from the approximation image $I_{i-1}$ and the back-projected corrective information;
   defining a new projection $p_i$ with the projection direction $\alpha_{gi}$ which differs, at least by approximation, by the angle $\alpha_g = g \cdot \alpha_{max}$ from the previous projection direction $\alpha_{gi}$, $\alpha_{max}$ representing the entire angular range used in creating the projections, and g representing the ratio of the golden section; and
   executing the iteration cycle until an abort condition is fulfilled.

* * * * *